United States Patent
Ishida et al.

(10) Patent No.: US 8,298,827 B2
(45) Date of Patent: Oct. 30, 2012

(54) METHOD FOR ANALYSIS OF METAL INCLUSIONS IN STEELS BY PARTIAL ELECTROLYSIS

(75) Inventors: Tomoharu Ishida, Chiba (JP); Satoshi Kinoshiro, Kanagawa (JP); Katsumi Yamada, Kanagawa (JP); Hisato Noro, Chiba (JP); Kaoru Sato, Kanagawa (JP)

(73) Assignee: JFE Steel Corporation (JP)

( * ) Notice: Subject to any disclaimer, the term of this patent is extended or adjusted under 35 U.S.C. 154(b) by 109 days.

(21) Appl. No.: 12/666,661

(22) PCT Filed: Jun. 26, 2008

(86) PCT No.: PCT/JP2008/062036
§ 371 (c)(1),
(2), (4) Date: Feb. 17, 2010

(87) PCT Pub. No.: WO2009/005111
PCT Pub. Date: Jan. 8, 2009

(65) Prior Publication Data
US 2010/0206736 A1 Aug. 19, 2010

(30) Foreign Application Priority Data

Jun. 29, 2007 (JP) .................................. 2007-171716
Jun. 23, 2008 (JP) .................................. 2008-162832

(51) Int. Cl.
*G01N 33/20* (2006.01)

(52) U.S. Cl. .......... 436/78; 436/73; 205/790; 205/790.5
(58) Field of Classification Search .................. None
See application file for complete search history.

(56) References Cited

U.S. PATENT DOCUMENTS
2005/0241956 A1 11/2005 Saini

FOREIGN PATENT DOCUMENTS

| JP | 56-010083 B | 3/1981 |
| JP | 58-119383 A | 7/1983 |
| JP | 59-141035 A | 8/1984 |
| JP | 08-184537 A | 7/1996 |
| JP | 2000-131313 A | 5/2000 |
| JP | 2001-159627 A | 6/2001 |

OTHER PUBLICATIONS

Rivas et al. "Electrochemical extraction of microalloy carbides in Nb-steel", Revista de Metalurgia, 2008, 44 (5), pp. 447-456.*

(Continued)

*Primary Examiner* — Yelena G Gakh
(74) *Attorney, Agent, or Firm* — DLA Piper LLP (US)

(57) ABSTRACT

A method for analyzing a metallic material includes the steps of electrolyzing a metal sample in an electrolyte; removing the electrolyzed metal sample from the electrolyte; immersing the metal sample removed from the electrolyte into a dispersive solution that is different from the electrolyte to separate at least one selected from the group consisting of a precipitate and an inclusion deposited on the metal sample; and analyzing the at least one selected from the group consisting of a precipitate and an inclusion extracted into the dispersive solution.

18 Claims, 6 Drawing Sheets

OTHER PUBLICATIONS

*The Japan Institute of Metals (Materia)*, 2006, vol. 45, No. 1, pp. 51-53 (original in Japanese) and 6 sheets (partial English translation).

Chino, A. et al., "New Developments in Methods for Inclusion and Precipitates Analysis," *Current Advances in Materials and Processes*, 2007, vol. 20, No. 3, 3 sheets (original in Japanese) and 4 sheets (partial English translation).

*The Iron and Steel Institute of Japan* (*Tekko Binran*), 4th edition (CD-ROM), vol. 4, section 2.3.5, 9 sheets (original in Japanese) and 1 sheet (partial English translation).

*Saishin no Tekko Jotai Bunseki* (*Agne Gijutsu Center*), 1989, pp. 58-59 and 62-63 (original in Japanese) and 2 sheets (partial English translation).

\* cited by examiner

METHOD FOR ANALYSIS OF METAL INCLUSIONS IN STEELS BY PARTIAL ELECTROLYSIS

RELATED APPLICATIONS

This is a §371 of International Application No. PCT/JP2008/062036, with an international filing date of Jun. 26, 2008 (WO 2009/005111 A1, published Jan. 8, 2009), which is based on Japanese Patent Application Nos. 2007-171716, filed Jun. 29, 2007, and 2008-162832, filed Jun. 23, 2008, the subject matter of which is incorporated by reference.

TECHNICAL FIELD

This disclosure relates to a method for accurately analyzing the composition and particle size distribution of a precipitate(s) and/or an inclusion(s) in a metal sample.

BACKGROUND

The shape, size, and distribution of a precipitate and/or an inclusion in a metal sample may greatly affect the characteristics of a material, for example, fatigue properties, hot workability and cold workability, deep drawability, machinability, or electromagnetic properties. A precipitate and/or an inclusion is hereinafter referred to as a precipitate or the like. For example, recent great advances in techniques for improving the characteristics of steel products utilizing a fine precipitate or the like have been associated with the increased precision with which the precipitate or the like is controlled in manufacturing processes.

Representative examples of steel products in which the control of a precipitate or the like is regarded as important include precipitation-hardened high-strength steel. Precipitates or the like contained in this precipitation-hardened high-strength steel sheet have various sizes and compositions. Precipitates can be classified into precipitates that can improve the properties of a steel sheet, precipitates that degrade the properties of a steel sheet, and precipitates that do not affect the properties of a steel sheet. To manufacture high-performance steel sheets, therefore, it is important to stably produce an advantageous precipitate or the like and prevent the formation of a disadvantageous or irrelevant precipitate or the like.

In general, advantages and disadvantages of a precipitate or the like to the properties of a steel sheet are closely related to the size of the precipitate or the like; the strength of a steel sheet increases with decreasing size of a precipitate or the like. Recently, steel sheets strengthened with a nano or sub-nano precipitate or the like have been developed. To determine the component design and manufacturing conditions of a steel sheet, therefore, it is important to determine the amount and the composition of a precipitate or the like for sizes in a submicron to nano range.

The quantitative determination of extracted precipitates or the like in a steel material has been developed and disclosed basically to evaluate the precipitates or the like as a whole.

The Iron and Steel Institute of Japan, "Tekko Binran, 4th edition (CD-ROM," Vol. 4, section 2.3.5 describes acidolysis, a halogen method, and electrolysis and reported that electrolysis is particularly suitable for a precipitate or the like. However, electrolysis described in The Iron and Steel Institute of Japan, "Tekko Binran, 4th edition (CD-ROM," Vol. 4, section 2.3.5 principally aims to aggregate a precipitate or the like in a liquid and recover the precipitate or the like by filtration, that is, to analyze the precipitate or the like as a whole. Thus, the size of the precipitate or the like cannot be determined. Furthermore, by the method described in The Iron and Steel Institute of Japan, "Tekko Binran, 4th edition (CD-ROM," Vol. 4, section 2.3.5, in a material containing a very small precipitate or the like, the precipitate or the like cannot be sufficiently aggregated, and part of the precipitate or the like passes through a filter. Thus, this method also has a problem with quantitative determination.

As a method for analyzing a chemically extracted non-metallic inclusion in a steel material according to size, Japanese Unexamined Patent Application Publication No. 59-141035 discloses a method for separating and collecting a precipitate or the like having at least a certain size by storing a steel sample placed in an electrolytic bath in a polytetrafluoroethylene net.

Japanese Examined Patent Application Publication No. 56-10083 discloses a technique for separating a precipitate or the like extracted in a liquid by filtration while applying ultrasonic waves to the precipitate or the like to prevent aggregation.

Basically, a precipitate or the like having a smaller particle size has a higher tendency to aggregate in a liquid. In the method described in Japanese Unexamined Patent Application Publication No. 59-141035, therefore, a precipitate or the like aggregates in a liquid in a manner that depends on the particle size. Thus, part of a precipitate or the like having a size smaller than the filter pore size is also trapped. This clearly leads to an inaccurate result of the size-specific analysis. Although aggregation does not cause a significant problem for an inclusion having a target size in the range of 50 to 1000 μm in Japanese Unexamined Patent Application Publication No. 59-141035, a precipitate or the like having a size in a submicron to nano range to which the greatest attention is paid, particularly of 1 μm or less in view of the control of the strength characteristics of steel, more desirably of 200 nm or less, is easily aggregated in a liquid in most cases. Thus, the method described in Japanese Unexamined Patent Application Publication No. 59-141035 is unsuited to practical use.

As in Japanese Unexamined Patent Application Publication No. 59-141035, Japanese Examined Patent Application Publication No. 56-10083 is also directed at a large precipitate or the like having a size of 1 μm or more, which is easy to aggregate and separate. Since the lower limit of sieving is generally 0.5 μm (see Agne Gijutsu Center, "Saishin no Tekko Jotai Bunseki," p. 58, 1979), the technique of Japanese Examined Patent Application Publication No. 56-10083 is difficult to apply to a precipitate or the like having a size in a submicron to nano range.

Japanese Unexamined Patent Application Publication No. 58-119383 discloses a technique for separating a precipitate or the like having a size of 1 μm or less with an organic filter having a pore size of 1 μm or less under ultrasonic vibration. However, as in Japanese Unexamined Patent Application Publication No. 59-141035 and Japanese Examined Patent Application Publication No. 56-10083, it is impossible to separate an aggregate of a fine precipitate or the like having a size of 1 μm or less with ultrasonic waves.

The Japan Institute of Metals, "Materia," Vol. 45, No. 1, p. 52, 2006 discloses a technique for extracting a precipitate or the like from a copper alloy and filtering the extract twice through filters having different pore sizes to separate the precipitate or the like according to size. However, the problem relating to aggregation described above is not solved, and part of a precipitate or the like having a size smaller than the filter pore size is also trapped, causing errors in the size-specific analysis results.

As described above, the related art has problems, such as aggregation, and there is no practical and accurate size-specific analysis technique of a precipitate or the like having a size in a submicron to nano range (particularly of 1 µm or less, more desirably of 200 nm or less).

It could therefore be helpful to provide an analysis method in which a precipitate and/or an inclusion, particularly having a size of 1 µm or less, in a metal sample is extracted without loss or aggregation and a size-specific analysis of the precipitate and/or the inclusion is precisely performed.

FIG. 9 shows the extraction procedure of electrolysis disclosed in The Iron and Steel Institute of Japan, "Tekko Binran, 4th edition (CD-ROM)," Vol. 4, section 2.3.5. In that electroextraction, a precipitate or the like in steel can be stably extracted by dissolving an iron matrix. The electroextraction is considered to be a standard method of an extraction analysis of a precipitate or the like (hereinafter referred to as a standard method). Japanese Unexamined Patent Application Publication Nos. 59-141035 and 58-119383 and Japanese Examined Patent Application Publication No. 56-10083 and Agne Gijutsu Center "Saishin no Tekko Jotai Bunseki," p. 58, 1979 and The Japan Institute of Metals, "Materia," Vol. 45, No. 1, p. 52, 2006 described above are based on this standard method. However, conventional methods, including the standard method, have various problems, as described above.

SUMMARY

We found that the problems of the conventional methods described above fundamentally result from the use of a poor dispersant, methanol, as a dispersion medium for a precipitate or the like. In particular, the use of a poor dispersant probably makes the size-specific analysis of a fine precipitate difficult. More specifically, in Japanese Unexamined Patent Application Publication Nos. 59-141035 and 58-119383 and Japanese Examined Patent Application Publication No. 56-10083 and The Iron and Steel Institute of Japan, "Tekko Binran, 4th edition (CD-ROM)," Vol. 4, section 2.3.5, Agne Gijutsu Center, "Saishin no Tekko Jotai Bunseki," p. 58, 1979 and The Japan Institute of Metals, "Materia," Vol. 45, No. 1, p. 52, 2006, the use of a poor dispersant, methanol, as a dispersion medium for a precipitate or the like causes aggregation of a precipitate or the like having a size of 1 µm or less even under a physical action, such as an ultrasonic wave, and it is probably impossible to completely separate the aggregate.

To solve the aggregation problem, we paid attention to the dispersion of a precipitate or the like and found that a chemical action of an aqueous dispersion medium (hereinafter also referred to as a "dispersive solution") allows a precipitate or the like, including a precipitate or the like having a size of 1 µm or less, to be dispersed.

However, because the main component of an electrolyte is a poor dispersant methanol, a precipitate or the like must be transferred to a dispersive solution to disperse the precipitate or the like. This requires solid-liquid separation between the precipitate or the like and the electrolyte. However, we found that "filtration" performed in the standard method as solid-liquid separation to recover part of a precipitate or the like dispersed in an electrolyte and part of the precipitate or the like extracted into a dispersion medium may result in a loss of part of the precipitate or the like (particularly having a nano or subnano size of 200 nm or less).

We found that substantially all the precipitate or the like is deposited on a steel sample during electrolysis and/or after electrolysis. This is a completely new finding. On the basis of this finding, solid-liquid separation can be easily performed by removing a remainder of a steel sample from an electrolyte during electrolysis and/or after electrolysis. We also found that these findings to solve the aggregation problem can be combined to allow extraction of a precipitate or the like into a dispersive solution, which is completely different from an electrolyte. Although the details of the deposition phenomenon described above are not clear, the deposition phenomenon may be caused by an electrical interaction between a steel sample and a precipitate or the like during electrolysis and/or after electrolysis.

We thus discovered that a highly dispersed precipitate or the like can be prepared by removing the remainder of a metal sample from an electrolyte during electrolysis or after electrolysis and directly immersing the metal sample into a dispersive solution to detach a precipitate or the like deposited on the metal sample in an aqueous dispersion medium.

We thus provide:

[1] A method for analyzing a metallic material, comprising the steps of:
  electrolyzing a metal sample in an electrolyte;
  removing the electrolyzed metal sample from the electrolyte;
  immersing the metal sample removed from the electrolyte into a dispersive solution that is different from the electrolyte to separate at least one selected from the group consisting of a precipitate and an inclusion deposited on the metal sample; and
  analyzing the at least one selected from the group consisting of a precipitate and an inclusion extracted into the dispersive solution.

[2] The method for analyzing a metallic material according to [1], wherein the dispersive solution contains water as a solvent.

[3] The method for analyzing a metallic material according to [1], wherein the dispersive solution has an absolute value of a zeta potential of 30 mV or more relative to at least one selected from the group consisting of a precipitate and an inclusion to be analyzed.

[4] The method for analyzing a metallic material according to [3], wherein the absolute value of a zeta potential ranges from 30 to 40 mV.

[5] The method for analyzing a metallic material according to [1], wherein at least one selected from the group consisting of type and concentration of the dispersive solution is determined using the zeta potential as an indicator.

[6] The method for analyzing a metallic material according to [1], wherein the dispersive solution contains, as a dispersing agent, one selected from the group consisting of sodium tartrate, sodium citrate, sodium silicate, tripotassium phosphate, sodium polyphosphate, sodium polymetaphosphate, sodium hexametaphosphate, and sodium diphosphate.

[7] The method for analyzing a metallic material according to [6], wherein the dispersive solution contains sodium hexametaphosphate as a dispersing agent.

[8] The method for analyzing a metallic material according to [6], wherein the dispersive solution contains sodium diphosphate as a dispersing agent.

[9] The method for analyzing a metallic material according to [1], wherein the separating step comprises applying ultrasonic vibration to the metal sample to detach at least one selected from the group consisting of a precipitate and an inclusion deposited on the metal sample.

[10] The method for analyzing a metallic material according to [1], wherein the analyzing step comprises analyzing at least one selected from the group consisting of a precipitate and an inclusion each having a size of 1 μm or less extracted into the dispersive solution.

[11] The method for analyzing a metallic material according to [1], further comprising the step of analyzing at least one selected from the group consisting of a precipitate and an inclusion deposited on the remainder of the metal sample.

[12] The method for analyzing a metallic material according to [1], wherein
the analyzing step comprises the substeps of:
filtering at least one selected from the group consisting of a precipitate and an inclusion separated into the dispersive solution at least once through at least one filter; and
analyzing at least one selected from the group consisting of a precipitate and an inclusion trapped by the at least one filter.

[13] The method for analyzing a metallic material according to [1], wherein
the analyzing step comprises the substeps of:
filtering at least one selected from the group consisting of a precipitate and an inclusion separated into the dispersive solution at least once through at least one filter; and
analyzing at least one selected from the group consisting of a precipitate and an inclusion in a filtrate.

[14] The method for analyzing a metallic material according to [1], wherein
the analyzing step comprises the substeps of:
filtering at least one selected from the group consisting of a precipitate and an inclusion separated into the dispersive solution at least once through at least one filter;
analyzing at least one selected from the group consisting of a precipitate and an inclusion trapped by the at least one filter; and
analyzing at least one selected from the group consisting of a precipitate and an inclusion in a filtrate.

[15] The method for analyzing a metallic material according to [13] or [14], wherein the filtrate analyzing step comprises analyzing at least one selected from the group consisting of a precipitate and an inclusion in the filtrate by multiplying a separately determined ratio of a target element to a labeled element in the electrolyte by a labeled element in the filtrate and subtracting the product from the amount of target element in the filtrate.

[16] The method for analyzing a metallic material according to [1], wherein the analyzing step comprises analyzing at least one selected from the group consisting of a precipitate and an inclusion in the dispersive solution by multiplying a separately determined ratio of a target element to a labeled element in the electrolyte by a labeled element in the dispersive solution and subtracting the product from the amount of target element in the dispersive solution.

BRIEF DESCRIPTION OF DRAWINGS

FIG. 3 is a schematic view of an electrolyzer for use in a method for analyzing a precipitate or the like.

DETAILED DESCRIPTION

The term "size," as used herein to express the size of an inclusion or the like, refers to the minor axis of the major axis and the minor axis of a generally circular cross section of a precipitate or the like or the short side of the long side and the short side of a rectangular cross section of a precipitate or the like. A precipitate or the like having a size of 1 μm or less refers to a precipitate or the like having a minor axis or a short side 1 μm or less in length. A precipitate and/or an inclusion is hereinafter collectively referred to as a precipitate or the like.

A precipitate or the like (particularly having a size of 1 μm or less, more desirably 200 nm or less) in a metal sample can be extracted without loss or aggregation, and the size-specific analysis of the precipitate or the like can be precisely performed.

Because a precipitate or the like (particularly having a size of 1 μm or less, more desirably 200 nm or less), in a metal sample is extracted into a dispersive solution, the aggregation of the precipitate or the like can be prevented in the extracting solution, and the precipitate or the like can be extracted while keeping the state in the metal sample.

Furthermore, because any extracting dispersive solution that is different from an electrolyte can be selected, a dispersive solution suitable for a precipitate or the like can be used.

Thus, a size-specific analysis of a precipitate or the like can be precisely performed, and the size-specific quantitative determination and the accurate determination of the particle size distribution, which were conventionally impossible, can be performed. Thus, our method can be industrially useful.

A method for analyzing metallic material will be described in detail below.

A method for analyzing metallic material includes the steps of electrolyzing a metal sample in an electrolyte; removing the electrolyzed metal sample from the electrolyte; immersing the metal sample removed from the electrolyte into a dispersive solution to separate at least one selected from the group consisting of a precipitate and an inclusion deposited on the metal sample; and analyzing the at least one selected from the group consisting of a precipitate and an inclusion extracted into the dispersive solution.

Figure 1:
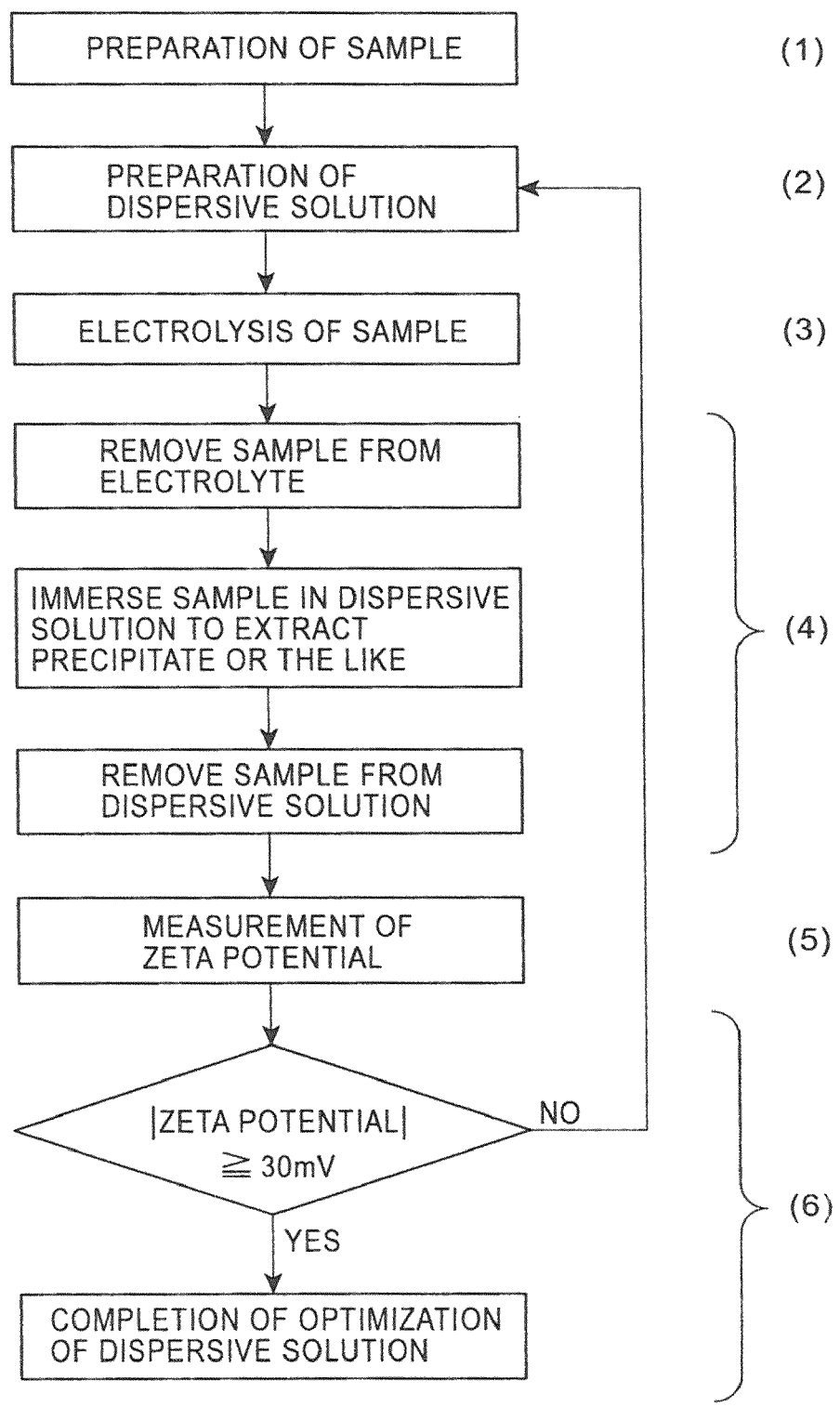
FIG. 1 is a flow chart of the determination of a dispersive solution.
Figure 2:
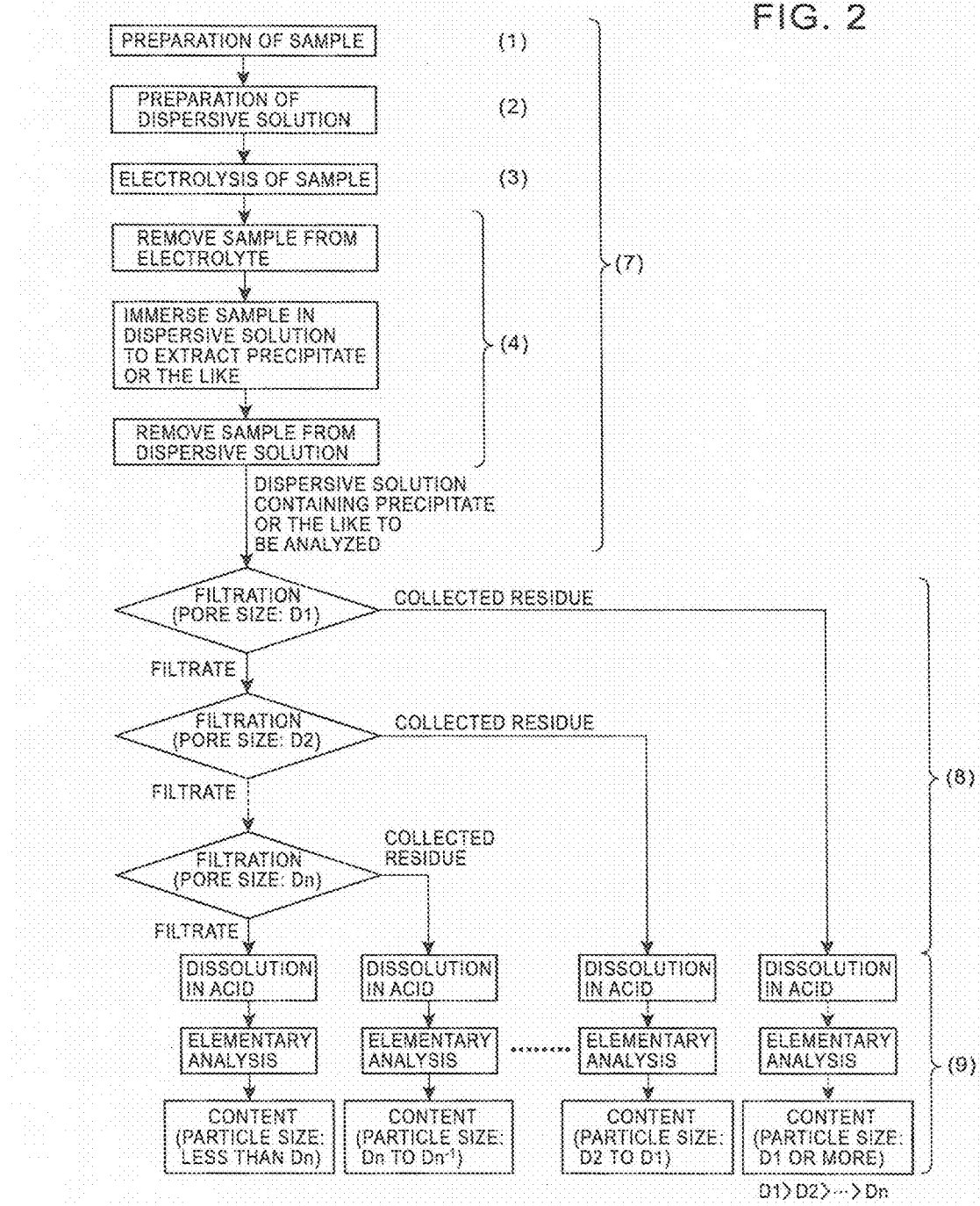
FIG. 2 is a flow chart of a size-specific quantitative analysis.

The steps up to the determination of a dispersive solution and the steps up to the size-specific quantitative determination of a precipitate or the like in a steel sample using a dispersive solution will be described below in an example. FIG. 1 is a flow chart of the determination of a dispersive solution. FIG. 2 is a flow chart of a size-specific quantitative determination of a precipitate or the like in a steel sample.

Figure 3:
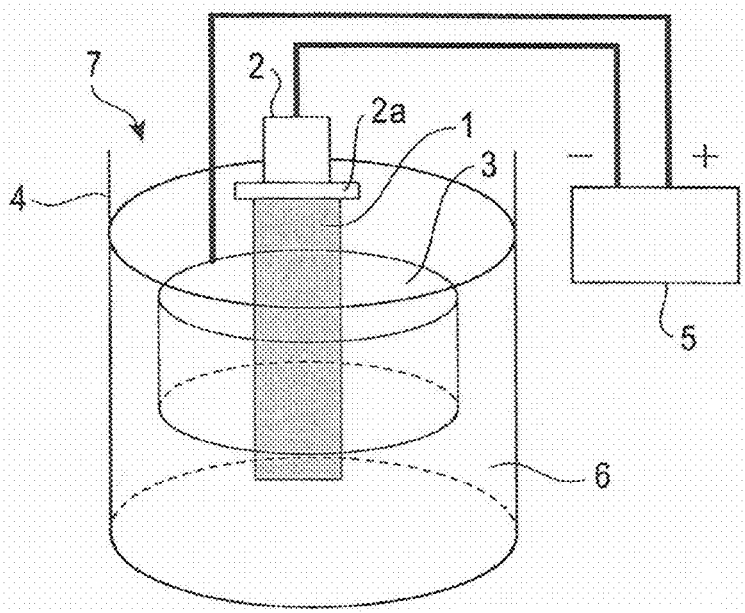

In FIG. 1, the dispersive solution conditions are determined through the following procedures (1) to (6):
- (1) First, a steel piece of an appropriate size is prepared as an electrolysis sample.
- (2) A dispersive solution for the extraction of a precipitate or the like, which is different from an electrolyte, is prepared separately from the electrolyte. An amount of the dispersive solution less than half that of the electrolyte is sufficient to disperse a precipitate or the like deposited on the surface of the electrolysis sample in the dispersive solution. A dispersing agent of the dispersive solution will be described below.
- (3) A certain amount of the sample is electrolyzed. The "certain amount" is appropriately determined and is, for example, measurable with a zeta potential apparatus (or an elementary analysis described below in (9)) in FIG. 1.
- FIG. 3 is an example of an electrolyzer for use in electrolysis. An electrolyzer 7 includes an electrolysis sample fixing device 2, an electrode 3, an electrolyte 6, a beaker 4 for containing the electrolyte 6, and a galvanostat 5 for supplying an electric current. The fixing device 2 is connected to an anode of the galvanostat, and the electrode 3 is connected to a cathode of a DC constant-current source. An electrolysis sample 1 is connected to the fixing device 2 and is held in the electrolyte 6. The electrode 3 is immersed in the electrolyte 6 and is placed to surround the surface of the electrolysis sample (mainly a portion of the electrolysis sample immersed in the electrolyte 6). Most conveniently, the fixing device 2 is formed of a permanent magnet. A portion of the fixing device 2 that may be exposed to the electrolyte 6, that is, a portion 2a adjacent to the electrolysis sample 1 in FIG. 3, may be formed of a platinum plate to prevent the fixing device 2 from being dissolved in the electrolyte 6. The electrode 3 is also formed of a platinum plate to prevent the electrode 3 from being dissolved in the electrolyte 6. The galvanostat 5 supplies electric charge to the electrode 3 to electrolyze the electrolysis sample 1. Because the amount of electrolyzed portion of steel is proportional to the amount of electric charge, the amount of electrolyzed portion of steel depends on the elapsed time at a given electric current.
- (4) An electrolysis sample remaining after electrolysis (dissolution) is removed from the electrolyzer and is immersed in the dispersive solution prepared in (2) to extract a precipitate or the like into the dispersive solution. Preferably, ultrasonic waves are applied to the electrolysis sample immersed in the dispersive solution. The application of ultrasonic waves can promote the detachment of a precipitate or the like from the surface of the sample, allowing the precipitate or the like to be extracted in the dispersive solution efficiently. The sample, from which the precipitate or the like is detached, is removed from the dispersive solution. When the sample is removed, the sample is preferably washed with the same solution as the dispersive solution.
- (5) The zeta potential of the dispersive solution containing a precipitate or the like prepared in (4) is measured.
- (6) If the absolute value of the zeta potential measured in (5) is less than 30 mV, the type and/or the concentration of a dispersing agent is altered, and (2) to (6) are performed again. If the zeta potential is 30 mV or more, the dispersing agent and its concentration are regarded as the optimum conditions of the dispersive solution for a target precipitate or the like. The procedures are thus completed. While the dispersing agent and its concentration are regarded as the optimum conditions of the dispersive solution for a target precipitate or the like if the zeta potential is 30 mV or more in FIG. 1, the dispersion of a precipitate and/or an inclusion in the dispersive solution without significant aggregation is considered satisfactory. The means for selecting the dispersive solution is not limited to the zeta potential measurement. Details will be described below.

FIG. 2 shows the following procedures (7) to (9) of the size-specific quantitative determination of a precipitate or the like in a steel sample using a dispersive solution:
- (7) The same procedures as (1) to (4) shown in FIG. 1 are performed again to extract a precipitate or the like to be analyzed into the dispersive solution determined by (1) to (6) shown in FIG. 1.
- (8) The dispersive solution containing a precipitate or the like is filtered through at least one filter, and a residue on the filter and a filtrate are collected. To divide a precipitate or the like into (n+1) fractions, a filtrate passing through a filter having a larger pore size is filtered through a filter having a smaller pore size, and this procedure is performed n times. Residues on the filters and an n-th filtrate are collected.
- (9) The residues on the filters and the filtrate are then independently dissolved in an acid and are subjected to elementary analysis to calculate the size-specific element contents of the precipitate or the like.

The size-specific composition of a precipitate or the like can be analyzed by the method shown in FIGS. 1 and 2. The analysis result can provide knowledge on the properties of steel and information useful in elucidating the cause of defects and developing a new material.

Our methods can be applied to various types of precipitates or the like in steel and is particularly suitable for steel materials that contain a large amount of precipitate or the like having a size of 1 μm or less, more suitable for steel materials that contain a large amount of precipitate or the like having a size of 200 nm or less.

The following is an additional description of the dispersive solution prepared in (2). As described above, there is no known method for extracting a fine precipitate or the like having a size of 1 μm or less, particularly 200 nm or less, without causing aggregation in a solution. Dispersing agents practically used for particles having a size of, for example, 1 μm or more were therefore tested to obtain information about a dispersive solution. The results showed that the type and the concentration of a dispersing agent had no clear correlation with the composition and the particle size of a precipitate or the like, and the density of a precipitate or the like in a liquid. For example, although sodium tartrate, sodium citrate, sodium silicate, tripotassium phosphate, sodium polyphosphate, sodium polymetaphosphate, sodium hexametaphosphate, and sodium diphosphate are suitable as aqueous dispersing agents, the addition of an excessive concentration of aqueous dispersing agent was counterproductive to the dispersion of a precipitate or the like.

Thus, the dispersive solution may be any dispersive solution provided that a precipitate and/or an inclusion is dispersed without aggregation in the dispersive solution. In the selection of the dispersive solution, preferably, the type and the concentration of the dispersive solution are appropriately determined in a manner that depends on the properties and the density of a precipitate or the like or the subsequent analytical method.

In a further investigation of the dispersive solution, it was found that, when the solvent of a dispersive solution is water, there is a close correlation between the surface charge of a precipitate or the like and dispersibility and that understanding the electric charge state of the surface of a precipitate or the like, for example, with a zeta potential analyzer allows the optimum conditions of the dispersive solution (the type of the dispersing agent and a suitable concentration of the dispersing agent added) to be determined. More specifically, because a smaller precipitate or the like has a higher tendency to aggregate in a liquid, it is believed that the addition of an appropriate concentration of an appropriate dispersing agent provides the surface of a precipitate or the like with electric charge, thus preventing aggregation by electrical repulsion.

In the determination of the type and the concentration of a dispersive solution, use of the zeta potential as an indicator seems desirable, because it is a simple and easy method and allows the optimum conditions of the dispersive solution (the type of the dispersing agent and a suitable concentration of the dispersing agent added) to be determined reliably.

As a result of repeated investigations, the developers found that the absolute value of the zeta potential is preferably as large as possible to disperse a precipitate or the like. We also found that the analysis of a precipitate or the like can be performed precisely without aggregation at an absolute value of approximately 30 mV or more.

Thus, the zeta potential is preferably used as an indicator to determine the type and the concentration of a dispersive solution for extracting a precipitate or the like. A dispersive solution preferably has an absolute value of a zeta potential of 30 mV or more relative to a precipitate and/or an inclusion to be analyzed.

Instead of the separation using at least one filter in (8), another separation method, such as electrophoresis or centrifugation, may be used to separate a precipitate or the like according to size, and each fraction of the precipitate or the like can be analyzed. The dispersive solution containing a precipitate or the like prepared in (7) may be directly analyzed. For example, the dispersive solution prepared in (7) can be subjected to dynamic light scattering or small-angle scattering to determine the particle size distribution of a precipitate or the like.

Instead of the elementary analysis and the quantitative analysis in (9), a residue on each filter can be analyzed by the X-ray diffraction to identify and perform qualitative analysis of a precipitate or the like according to particle size. A residue on each filter can be directly subjected to an analyzer, such as a scanning electron microscope (SEM), a transmission electron microscope (TEM), an electron probe micro analyzer (EPMA), or an X-ray photoelectron micro analyzer (XPS), for observation of the shape or the surface analysis of a precipitate or the like. A filtrate passing through the filters can be subjected to dynamic light scattering or small-angle scattering to measure the size after the separation with the filters.

When a target element forms a very fine precipitate or the like on the order of a few nanometers in a metallic material, a solid solution portion and a precipitate portion of the target element sometimes cannot be separated, causing errors in the analytical value of the precipitate or the like, as indicated by The Japan Institute of Metals, "Materia," Vol. 45, No. 1, p. 52, 2006. More specifically, the solid solution portion of the target element is eluted into an electrolyte by an extraction procedure, such as electrolysis. Part of the eluted solid solution portion is deposited on the surface of a sample and is introduced into the dispersive solution in (4) together with a precipitate or the like, causing a positive error in the analysis result of a precipitate or the like in the dispersive solution in (4) or in the filtrate of the dispersive solution in (8). We focused on the point that the error is caused by the electrolyte and found that an analysis result with a reduced error can be obtained by quantifying the contamination level and subtracting the contamination level from the apparent analytical value of a precipitate or the like.

The method will be described below. A proper amount of electrolyte is collected after electrolysis, and the amount Ci of target element and the amount Ct of labeled element in the electrolyte are measured to calculate the ratio Ci/Ct. The amount of target element introduced from the electrolyte in the dispersive solution in (4) or in the filtrate of the dispersive solution in (8) was quantified by measuring the amount Xt of labeled element in the dispersive solution in (4) or in the filtrate of the dispersive solution in (8) and multiplying the amount Xt by the ratio Ci/Ct. A net precipitate analytical value Wi of target element derived from a precipitate can be obtained by subtracting the introduced amount from the amount Xi of target element in the dispersive solution in (4) or in the filtrate of the dispersive solution in (8);

$$Wi = (Xi - Xt \times Ci/Ct) \times 100/M \tag{1}$$

Wi: the precipitate analytical value of a target component in a sample (% by mass)

Xi: the mass of a target element in a precipitate dispersion or in a filtrate of the dispersion Xt: the mass of a labeled element in a precipitate dispersion or in a filtrate of the dispersion Ci: the mass per unit volume of a target element in a collected electrolyte Ct: the mass per unit volume of a labeled element in a collected electrolyte M: the weight of an electrolyzed portion of a sample.

The labeled element is either of the following two types. First, the labeled element is an element that is contained in a sample and forms little or no precipitate or the like. For example, iron or nickel is suitable for steel samples. Alternatively, the labeled element is an element that is not substantially contained in a sample and is added to an electrolyte. Lithium, yttrium, or rhodium is suitable for steel samples.

Example 1

According to the procedures (1) to (6) shown in FIG. 1, the relationship between the titanium content of a precipitate or the like and the zeta potential was investigated. The specific conditions of the procedures will be described below. Our methods are not limited to these specific conditions.

Carbon steel containing titanium was used as a metal sample. The chemical components of the carbon steel are C: 0.09% by mass, Si: 0.12% by mass, Mn: 1.00% by mass, P: 0.010% by mass, S: 0.003% by mass, Ti: 0.18% by mass, and N: 0.0039% by mass.

Electrolysis was performed in an electrolyzer illustrated in FIG. 3 using approximately 300 ml of 10% AA electrolyte (10% by volume of acetylacetone-1% by mass of tetramethylammonium chloride-methanol) as an electrolyte.

The dispersive solution was aqueous sodium hexametaphosphate (hereinafter abbreviated as SHMP). The SHMP concentration was altered at seven levels in the range of 0 to 2000 mg/l.

Under these conditions, the procedures (1) to (5) shown in FIG. 1 were performed, and the zeta potential was measured with a zeta potential analyzer under each condition.

Figure 4:
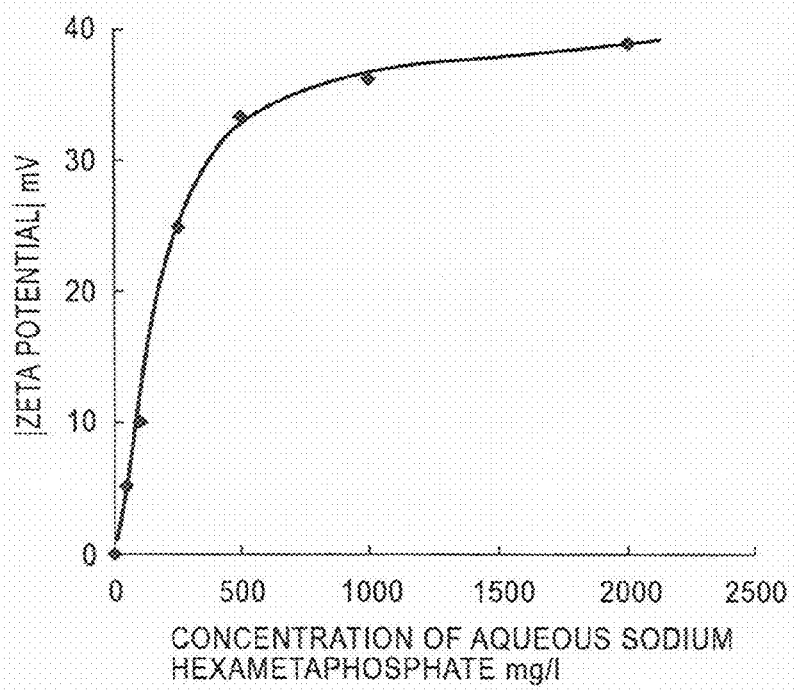
FIG. 4 is a graph showing the relationship between the concentration of aqueous sodium hexametaphosphate and the zeta potential of a dispersive solution.

FIG. 4 shows the result. FIG. 4 shows that the absolute value of the zeta potential increases with increasing SHMP concentration. When the same experiment was performed using aqueous sodium diphosphate as the dispersive solution, the result had the same tendency as in FIG. 4.

Figure 5:
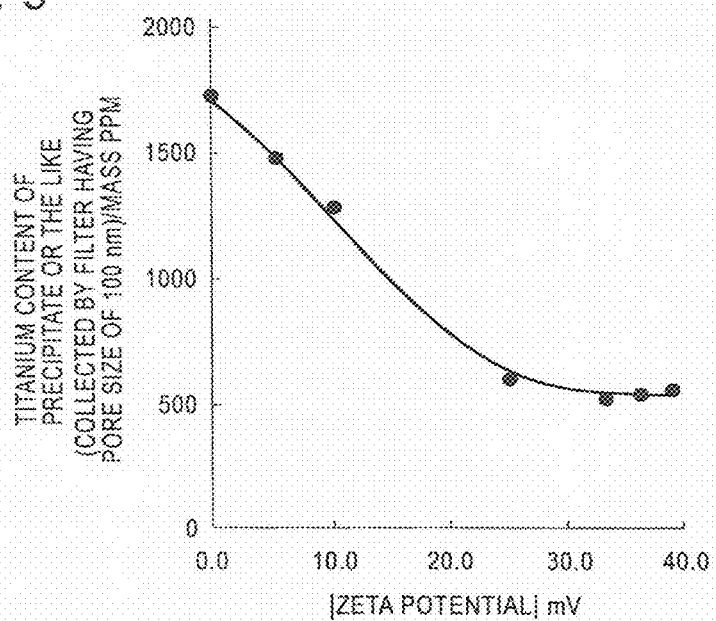
FIG. 5 is a graph showing the relationship between the zeta potential and the titanium content of a precipitate or the like collected with a filter having a pore size of 100 nm.

The procedures (7) to (9) shown in FIG. 2 were then performed using the seven aqueous SHMP solutions described above as the dispersive solution to analyze titanium in a precipitate or the like. FIG. 5 shows the result. In FIG. 5, the titanium content is expressed relative to 100% by mass of all the components of the sample. In the procedure (8), the filter pore size was 100 nm.

FIG. 5 shows that the titanium content of a precipitate or the like having a size of 100 nm or more was high at a small absolute value of the zeta potential, indicating that the titanium content of a precipitate or the like having a size of 100 nm or more was apparently high owing to the aggregation of the precipitate or the like. At an absolute value of the zeta potential of approximately 30 mV or more, the titanium content of a precipitate or the like having a size of 100 nm or more was almost constant, and the result of a size-specific analysis of a precipitate or the like was not changed. Thus, it has been concluded that dispersibility was substantially satisfactory at an absolute value of the zeta potential of 30 mV or more.

Example 2

In Example 2, the analysis of the titanium content of a precipitate or the like in steel is more specifically described using an analysis method (working example) and methods according to The Iron and Steel Institute of Japan, "Tekko Binran, 4th edition (CD-ROM)," Vol. 4, section 2.3.5 and Japanese Unexamined Patent Application Publication No. 58-119383 (Comparative Examples 1 and 2).

A steel ingot having a composition shown in Table 1 was cut into three samples: sample A, sample B, and sample C. The sample A was heated at 1250° C. for 60 min and was then water-cooled. The samples B and C were heated at 1250° C. for 60 min, were rolled at a finishing temperature of 950° C., and were heat-treated under the conditions shown in Table 2. After cooling, the samples A, B, and C were cut into an appropriate size and were sufficiently surface-ground. For each of the samples, the titanium content of a precipitate or the like in steel (relative to 100% by mass of all the components shown in Table 1) was analyzed by our analysis method (working example), a method according to The Iron and Steel Institute of Japan, "Tekko Binran, 4th edition (CD-ROM)," Vol. 4, section 2.3.5 (Comparative Example 1), and a method according to Japanese Unexamined Patent Application Publication No. 58-119383 (Comparative Example 3). These analysis methods will be described in detail below. Table 2 shows the approximate size of a precipitate or the like in the samples, as determined by electron microscopy.

TABLE 1

| (% by mass) | | | | |
| --- | --- | --- | --- | --- |
| C | Si | Mn | Ti | N |
| 0.08 | 0.5 | 1.00 | 0.09 | 0.0030 |

TABLE 2

| | Heating conditions | | |
| --- | --- | --- | --- |
| Sample | Temperature (° C.) | Time (min) | Outline of precipitate or the like observed with electron microscope |
| Sample A | — | — | Precipitate or the like 1 μm or more in size |
| Sample B | 650 | 1 | Precipitate or the like 1 μm or more in size and precipitate or the like approximately 2 nm in size |
| Sample C | 650 | 300 | Precipitate or the like 1 μm or more in size and precipitate or the like approximately 10 nm in size |

Table 2 shows that the sample A produced a precipitate or the like having an ordinary size. The samples B and C produced a fine precipitate or the like having a size on the order of nanometers. In particular, the sample B produced a fine precipitate or the like having the smallest size of approximately 2 nm.

Working Example

Our Analysis Method

First, approximately 0.5 g of the steel sample previously weighed with a balance used as an anode was electrolyzed at a constant potential using approximately 300 ml of 10% AA electrolyte.

After turning off the electricity, the sample was slowly removed from the electrolyte and was placed in an container that contained approximately 100 ml of aqueous SHMP (concentration of 500 mg/l). Ultrasonic vibration was applied to the sample to detach a precipitate or the like deposited on the surface of the sample in the container, thus extracting the precipitate or the like into the aqueous SHMP. When the surface of the sample had a metallic luster, the ultrasonic vibration was stopped. The sample was removed from the container, was washed with 500 mg/l aqueous SHMP and pure water, and was dried. After drying, the sample weight was measured with a balance. The weight of an electrolyzed portion of the sample was calculated by subtracting the sample weight measured after the electrolysis from the sample weight measured before the electrolysis.

The dispersion of a precipitate or the like in the container was filtered by suction filtration through a filter having a pore size of 100 nm to collect a residue on the filter. The residue, together with the filter, was dissolved in a hot mixture of nitric acid, perchloric acid, and sulfuric acid. The resulting solution was analyzed with an ICP spectrometer to determine the absolute amount of titanium in the residue. The absolute amount of titanium in the residue was divided by the weight of an electrolyzed portion of the sample to calculate the titanium content of a precipitate or the like having a size of 100 nm or more.

The filtrate passing through the filter having a pore size of 100 nm was heated on a hot plate at 80° C. The resulting dry residue was dissolved in a hot mixture of nitric acid, perchloric acid, and sulfuric acid. The resulting solution was analyzed with an ICP spectrometer to determine the absolute amount of titanium in the filtrate. The absolute amount of titanium in the filtrate was divided by the weight of an electrolyzed portion of the sample to calculate the titanium content of a precipitate or the like having a size below 100 nm.

Comparative Example 1

Method According to The Iron and Steel Institute of Japan, "Tekko Binran, 4th Edition (CD-ROM)," Vol. 4, Section 2.3.5

The procedures (7) to (9) shown in FIG. 2 were performed. First, approximately 0.5 g of the steel sample previously weighed with a balance used as an anode was electrolyzed at a constant potential using approximately 300 ml of 10% AA electrolyte.

After turning off the electricity, the sample was slowly removed from the electrolyte was placed in an container that contained approximately 100 ml of methanol. Ultrasonic vibration was applied to the sample to detach a precipitate or the like deposited on the surface of the sample in the container, thus extracting the precipitate or the like into the methanol. When the surface of the sample had a metallic luster, the ultrasonic vibration was stopped. The sample was removed from the container, was washed with methanol, and was dried. After drying, the sample weight was measured with a balance. The weight of an electrolyzed portion of the sample was calculated by subtracting the sample weight measured after the electrolysis from the sample weight measured before the electrolysis.

The electrolyte and the methanol in which a precipitate or the like was dispersed in the container were filtered by suction filtration through a filter having a pore size of 100 nm to collect a residue on the filter. The residue, together with the filter, was dissolved in a hot mixture of nitric acid, perchloric acid, and sulfuric acid. The resulting solution was analyzed with an ICP spectrometer to determine the absolute amount of titanium in the residue. The absolute amount of titanium in the residue was divided by the weight of an electrolyzed portion of the sample to calculate the titanium content of a precipitate or the like having a size of 100 nm or more.

Comparative Example 3

Method According to Japanese Unexamined Patent Application Publication No. 58-119383

Approximately 0.5 g of the steel sample previously weighed with a balance used as an anode was electrolyzed at a constant potential using approximately 300 ml of 10% AA electrolyte.

After turning off the electricity, the sample was slowly removed from the electrolyte and was placed in an container that contained approximately 100 ml of methanol. Ultrasonic vibration was applied to the sample to detach a precipitate or the like deposited on the surface of the sample in the container. When the surface of the sample had a metallic luster, the ultrasonic vibration was stopped. The sample was removed from the container, was washed with methanol, and was dried. After drying, the sample weight was measured with a balance. The weight of an electrolyzed portion of the sample was calculated by subtracting the sample weight measured after the electrolysis from the sample weight measured before the electrolysis.

The electrolyte and the methanol in which a precipitate or the like was dispersed in the container were filtered by suction filtration through a filter having a pore size of 100 nm in a filtering apparatus provided with an ultrasonic transducer while ultrasonic waves were applied, thus collecting a residue on the filter. The residue, together with the filter, was dissolved in a hot mixture of nitric acid, perchloric acid, and sulfuric acid. The resulting solution was analyzed with an ICP spectrometer to determine the absolute amount of titanium in the residue. The absolute amount of titanium in the residue was divided by the weight of an electrolyzed portion of the sample to calculate the titanium content of a precipitate or the like having a size of 100 nm or more.

Figure 6:
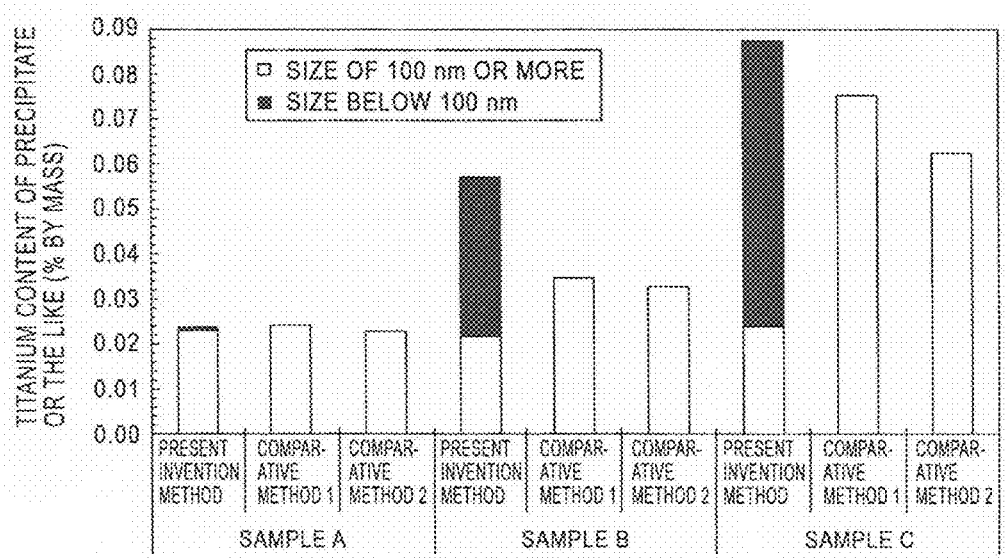
FIG. 6 is a graph of the size-specific quantitative determination of a titanium precipitate or the like in Example 2.

FIG. 6 shows the titanium contents of a precipitate or the like in the working example, Comparative Example 1, Comparative Example 2. FIG. 6 demonstrated the following.

First, the titanium contents of a precipitate or the like having a size of 100 nm or more determined by these analysis methods are compared. For the sample A, the titanium contents of a precipitate or the like having a size of 100 nm or more are almost the same. This is because the sample A contains no fine precipitate or the like. For the samples B and C, the titanium content of a precipitate or the like having a size of 100 nm or more is much higher in Comparative Examples 1 and 2 than in the working example. This is because a fine precipitate or the like contained in the samples B and C aggregated in the solution after extraction under conditions of Comparative Examples 1 and 2 and was collected by the filter having a pore size of 100 nm, causing a positive error in the analytical value.

The titanium contents of a precipitate or the like having a size of 100 nm or more of the samples A, B, and C in the working example are compared. The titanium contents of a precipitate or the like having a size of 100 nm or more of the samples A, B, and C in the working example are almost the same. This is because a large precipitate or the like is formed during the solidification of molten steel and is not changed by such a low-temperature treatment as in the working example. Thus, the same titanium contents of a precipitate or the like having a size of 100 nm or more of the samples A, B, and C prepared from the same steel ingot in our method are very reasonable results, indicating that the samples are properly analyzed without contamination of a fine precipitate or the like.

Finally, the titanium content of a precipitate or the like having a size below 100 nm in the working example is discussed below. In the sample C, the total titanium content of precipitates or the like (having sizes below 100 nm and 100 nm or more) in the working example is the same as the titanium content of steel (0.09% by mass). In the working example, therefore, almost all the titanium precipitate or the like was analyzed without a significant loss. In consideration of the reasonable titanium content of a precipitate or the like having a size of 100 nm or more described above, the titanium content of a precipitate or the like having a size below 100 nm in the working example is also reasonable.

A filtrate passing through a filter having a pore size of 100 nm in the sample C was filtered through a filter having a pore size of 50 nm. The titanium contents of a residue collected on the filter having a pore size of 50 nm and a filtrate passing through the filter having a pore size of 50 nm were measured in the same manner as in the measurement of the titanium content of a precipitate or the like having a size of 100 nm or more. The titanium content of a precipitate or the like having a size below 50 nm was 0.061% by mass, and the titanium content of a precipitate or the like having a size of 50 nm or more but less than 100 nm was 0.003% by mass.

Example 3

The particle size distribution was determined following the procedures (1) to (4) shown in FIG. 2.

Carbon steel was used as a metal sample. The chemical components of the carbon steel are C: 0.10% by mass, Si: 0.2% by mass, Mn: 1.0% by mass, P: 0.024% by mass, S: 0.009% by mass, Cr: 0.03% by mass, and Ti: 0.05% by mass. An electrolysis sample having a size of 20 mm×50 mm×1 mm was cut from the carbon steel.

Electrolysis was performed in an electrolyzer illustrated in FIG. 3 using 500 ml of 10% AA electrolyte as an electrolyte. The amount of electrolyzed portion of steel was 0.1 g per electrolysis treatment. The procedures (3) and (4) were performed 10 times. Sacrificial electrolysis for removing contaminants on the surface was performed once immediately before electrolysis.

Figure 7:
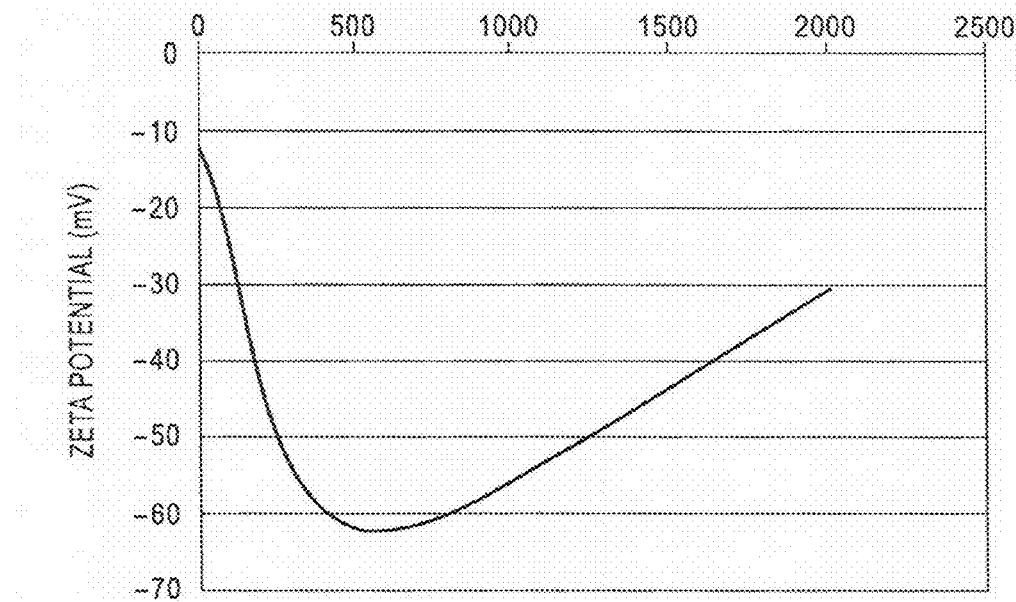
FIG. 7 is a graph showing the relationship between the concentration of aqueous sodium hexametaphosphate and the zeta potential of a dispersive solution in Example 3.

The dispersive solution was 500 mg/l aqueous sodium hexametaphosphate, 50 ml of which was prepared in a beaker separated from the electrolyzer. The optimum concentration of sodium hexametaphosphate was previously determined by measuring the zeta potential with a zeta potential analyzer. FIG. 7 shows an example of the relationship between the concentration of sodium hexametaphosphate and the zeta potential previously measured. FIG. 7 shows that, in the present example, although the absolute value of the zeta potential was largest when 500 mg/l aqueous sodium hexametaphosphate was used as a dispersion medium, the final particle size was not altered even at a concentration of 2000 mg/l. Thus, it has been concluded that dispersibility is substantially excellent at an absolute value of the zeta potential of 30 mV or more.

Figure 8:
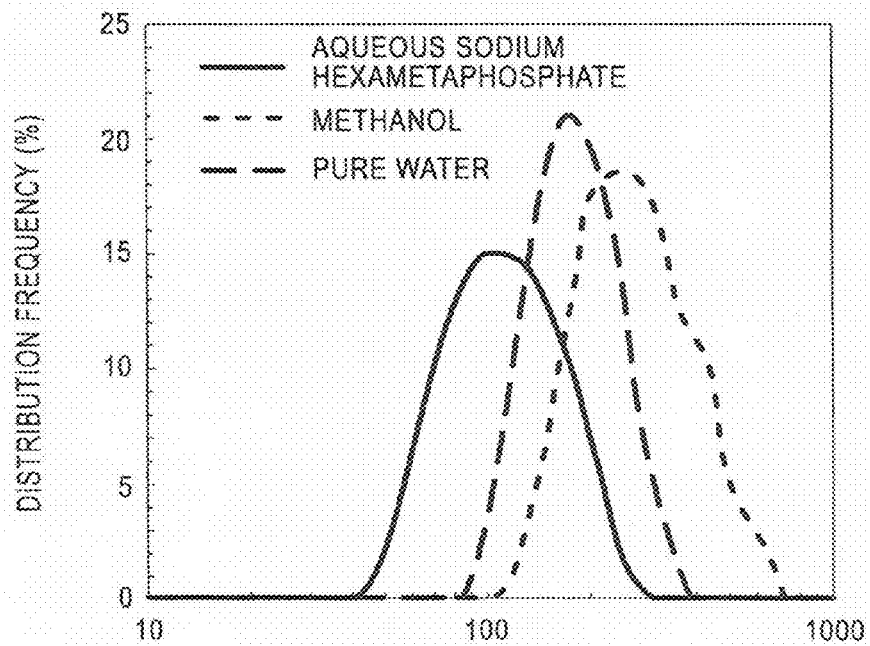
FIG. 8 is a graph showing the measurements of the particle size distribution in Example 3.
Figure 9:
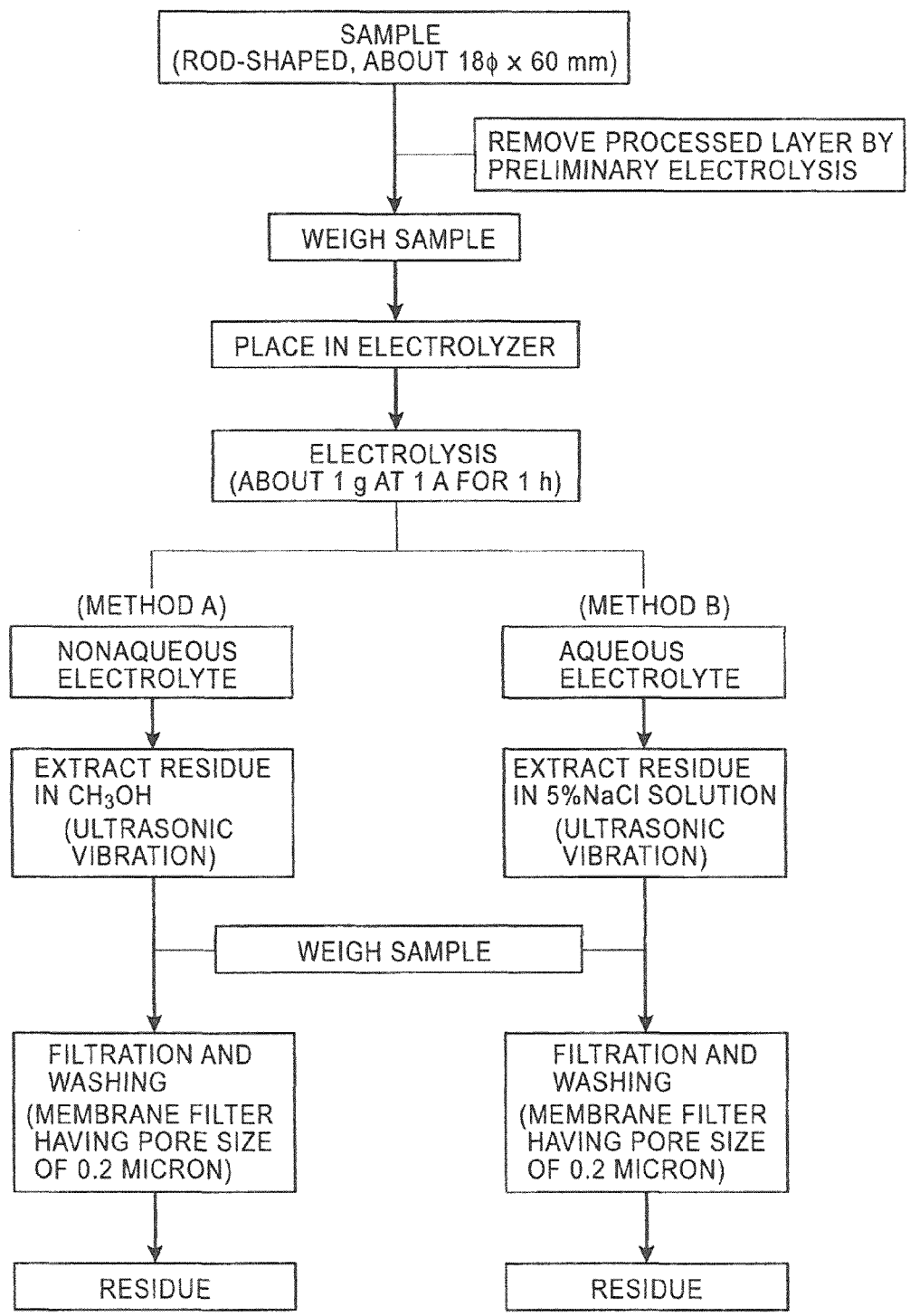
FIG. 9 is a flow chart of a standard method disclosed in The Iron and Steel Institute of Japan, "Tekko Binran, 4th edition (CD-ROM)," Vol. 4, section 2.3.5.

Subsequently, while ultrasonic waves were applied, the dispersive solution was agitated with a magnet bar to remove cementite or the like. While ultrasonic waves were applied, the dispersive solution was then filtered through a filter having a pore size of 0.4 μm to remove precipitates or the like that are not to be analyzed. The resulting filtrate (dispersive solution containing a precipitate or the like) was used to determine the particle size distribution of a precipitate or the like in the dispersive solution with a dynamic light scattering particle size distribution analyzer. FIG. 8 shows the result.

FIG. 8 also shows the particle size distributions of precipitates or the like collected in methanol and pure water as Comparative Examples. The zeta potential of a precipitate or the like in methanol could not be measured because of the inconvenience of equipment. The zeta potential of a precipitate or the like in pure water was −11 mV.

FIG. 8 shows that the particle size distribution of a precipitate or the like in a dispersive solution of 500 mg/l aqueous sodium hexametaphosphate was consistent with the direct observation with an electron microscope of a precipitate or the like deposited on the surface after electrolysis. This demonstrates that a precipitate or the like can be dispersed in a liquid without aggregation. Thus, according to our method, a fine precipitate or the like, which is conventionally difficult to prevent aggregation in a liquid, can be extracted in a dispersed state. The status of a precipitate or the like in steel can therefore be evaluated accurately.

Example 4

The analysis of a titanium precipitate or the like and a manganese precipitate or the like in a steel material shown in Table 3 will be specifically described in the following examples.

TABLE 3

| (% by mass) | | | | |
|---|---|---|---|---|
| C | Mn | S | Ti | N |
| 0.08 | 2.0 | 0.003 | 0.05 | 0.0030 |

Working Example

In the working example, iron, which was an element contained in a sample, and rhodium, which was an element that was not contained in a sample and was intentionally added to the sample, were used as labeled elements.

Approximately 300 ml of 10% AA electrolyte (10% by volume of acetylacetone-1% by mass of tetramethylammonium chloride-methanol) was used as an electrolyte. 20 mg of rhodium acetylacetonate is added to the electrolyte and was stirred sufficiently. Approximately 0.5 g of the steel sample is electrolyzed at a constant potential in the electrolyte. After electrolysis, the sample on which a residue was deposited was removed from the electrolyte and was placed in an container that contained approximately 100 ml of aqueous SHMP (concentration of 500 mg/l). Ultrasonic vibration was applied to the sample to detach a precipitate or the like deposited on the surface of the sample in the container, thus extracting the precipitate or the like into the aqueous SHMP. When the surface of the sample had a metallic luster, the ultrasonic vibration was stopped. The sample was removed from the container, was washed with 500 mg/l aqueous SHMP and pure water, and was dried. After drying, the sample weight was measured with a balance. The weight M of an electrolyzed portion of the sample was calculated by subtracting the sample weight measured after the electrolysis from the sample weight measured before the electrolysis. The aqueous SHMP in which a precipitate or the like was detached was passed through a filter having a pore size of 100 nm to collect a filtrate. The filtrate was dried, was then dissolved in hot nitric acid and another liquid, and was analyzed with an ICP spectrometer or an ICP mass spectrometer to determine the titanium content (XTi) and the manganese content (XMn) as target elements and the iron content (XFe) and the rhodium content (XRh) as labeled elements.

After electrolysis, approximately 1 ml of electrolyte was dried. A residue was dissolved in hot nitric acid and was analyzed with an ICP mass spectrometer to determine the titanium content (CTi), the manganese content (CMn), the iron content (CFe), and the rhodium content (CRh) in the solution.

These results were substituted into the equation (1) to calculate the contents (WTi and WMn) of a titanium precipitate or the like and a manganese precipitate or the like each having a size below 100 nm in steel when iron and rhodium were used as labeled elements.

Comparative Example

Approximately 300 ml of 10% AA electrolyte (10% by volume of acetylacetone-1% by mass of tetramethylammonium chloride-methanol) was used as an electrolyte. Approximately 0.5 g of the steel sample is electrolyzed at a constant potential in the electrolyte. After electrolysis, the sample on which a residue was deposited was removed from the electrolyte and was placed in an container that contained approximately 100 ml of aqueous SHMP (concentration of 500 mg/l). Ultrasonic vibration was applied to the sample to detach a precipitate or the like deposited on the surface of the sample in the container, thus extracting the precipitate or the like into the aqueous SHMP. When the surface of the sample had a metallic luster, the ultrasonic vibration was stopped. The sample was removed from the container, was washed with 500 mg/l aqueous SHMP and pure water, and was dried. After drying, the sample weight was measured with a balance. The weight M of an electrolyzed portion of the sample was calculated by subtracting the sample weight measured after the electrolysis from the sample weight measured before the electrolysis. The aqueous SHMP in which a precipitate or the like was detached was passed through a filter having a pore size of 100 nm to collect a filtrate. The filtrate was dried, was then dissolved in hot nitric acid and another liquid, and was analyzed with an ICP spectrometer or an ICP mass spectrometer to determine the titanium content (XTi) and the manganese content (XMn) as target elements. These results were substituted into the following equations to calculate the contents (WTi and WMn) of a titanium precipitate or the like and a manganese precipitate or the like each having a size below 100 nm in steel:

WTi=XTi/M

WMn=XMn/M.

Table 4 shows the contents of a titanium precipitate or the like and a manganese precipitate or the like each having a size below 100 nm measured in the working example (iron or rhodium as a labeled element) and Comparative Example. Analytical values for the titanium precipitate or the like show little difference among the methods. However, for the manganese precipitate or the like, the result of Comparative Example was higher than the results of the working example. Manganese in steel mostly forms solid solution with iron in the matrix. After electrolysis, therefore, a very large amount of manganese is eluted into the electrolyte. Manganese deposited on the sample and introduced into the electrolyte is finally introduced into the filtrate, causing a positive error in the analysis result of a manganese precipitate or the like. The positive error resulted in the high analytical value of a manganese precipitate or the like in Comparative Example. In the working example, the introduced manganese was compensated by the labeled element, thus providing the accurate analysis result without a positive error. Use of iron, an element contained in the sample, as a labeled element conveniently eliminates the need for the addition of a labeled element, but may result in the presence of a precipitate or the like formed of the labeled element, such as cementite, in a filtrate. This resulted in excessive compensation and a slightly low analytical value. For the titanium precipitate or the like, the analysis results show little difference among the methods. This is because titanium in steel mostly forms a precipitate or the like, that is, the titanium content of the electrolyte is low, and no compensation effect is produced.

These results demonstrated the accuracy of the analysis result obtained by our method.

TABLE 4

|  | Labeled element | Analysis result of a precipitate or the like having a size below 100 nm (ppm) | |
|---|---|---|---|
|  |  | Ti | Mn |
| Example | Iron | 340 | 10 |
|  | Rhodium | 337 | 14 |
| Comparative Example | None | 342 | 45 |

What is claimed is:

1. A method for analyzing at least one of metal precipitates and inclusions within a steel material, comprising the steps of:
    partially electrolyzing a sample of the steel material in an electrolyte wherein at least one of the metal precipitates and inclusions attach to a remaining portion of the sample during or after electrolysis;
    removing the remaining portion of the sample from the electrolyte with the metal inclusions and precipitates attached thereto;
    immersing the remaining portion of the sample removed from the electrolyte into a dispersive solution that does not contain methanol and is different from the electrolyte to separate at least one of the metal precipitates and the inclusions attached to the sample wherein the dispersive solution disperses aggregates of the precipitates and inclusions;
    filtering at least one of the metal precipitates or inclusions separated into the dispersive solution through at least one filter; and
    analyzing the at least one of the metal precipitates and inclusions.

2. The method according to claim 1, wherein the dispersive solution contains water as a solvent.

3. The method according to claim 1, wherein the dispersive solution has an absolute value of a zeta potential of 30 mV or more relative to at least one selected from the group consisting of a metal precipitate and a metal inclusion to be analyzed.

4. The method according to claim 3, wherein the absolute value of a zeta potential ranges from 30 to 40 mV.

5. The method according to claim 1, wherein at least one selected from the group consisting of type and concentration of the dispersive solution is determined using the zeta potential as an indicator.

6. The method according to claim 1, wherein the dispersive solution contains, as a dispersing agent, one selected from the group consisting of sodium tartrate, sodium citrate, sodium silicate, tripotassium phosphate, sodium polyphosphate, sodium polymetaphosphate, sodium hexametaphosphate, and sodium diphosphate.

7. The method according to claim 6, wherein the dispersive solution contains sodium hexametaphosphate as a dispersing agent.

8. The method according to claim 6, wherein the dispersive solution contains sodium diphosphate as a dispersing agent.

9. The method according to claim 1, wherein the separating step comprises applying ultrasonic vibration to the remaining portion of the sample to detach at least one of the metal precipitates and the metal inclusions.

10. The method according to claim 1, wherein the analyzing step comprises analyzing at least one of the metal precipitates and the metal inclusions each having a size of 1 μm or less extracted into the dispersive solution.

11. The method according to claim 1, further comprising the step of analyzing at least one of the metal precipitates and the metal inclusions deposited on the remaining portion of the sample.

12. The method according to claim 1, wherein
    the analyzing step comprises the substeps of:
    filtering at least one of the metal precipitates and the metal inclusions separated into the dispersive solution at least once through at least one filter; and
    analyzing at least one of the metal precipitates and the metal inclusions trapped by the at least one filter.

13. The method according to claim 1, wherein
    the analyzing step comprises the substeps of:
    filtering at least one of the metal precipitates and the metal inclusions separated into the dispersive solution at least once through at least one filter; and
    analyzing at least one of the metal precipitates and the metal inclusions in a filtrate.

14. The method according to claim 13, wherein the filtrate analyzing step comprises analyzing at least one of the metal precipitates and the metal inclusions in the filtrate by multiplying a separately determined ratio of a target element to a labeled element in the electrolyte by a labeled element in the filtrate and subtracting the product from the amount of target element in the filtrate.

15. The method according to claim 1, wherein
the analyzing step comprises the substeps of:
filtering at least one of the metal precipitates and the metal inclusions separated into the dispersive solution at least once through at least one filter;
analyzing at least one of the metal precipates and the metal inclusions trapped by the at least one filter; and
analyzing at least one of the metal precipitates and the metal inclusions in a filtrate.

16. The method according to claim 15, wherein the filtrate analyzing step comprises analyzing at least one of the metal precipitates and the metal inclusions in the filtrate by multiplying a separately determined ratio of a target element to a labeled element in the electrolyte by a labeled element in the filtrate and subtracting the product from the amount of target element in the filtrate.

17. The method according to claim 1, wherein the analyzing step comprises analyzing at least one of the metal precipitates and the metal inclusions in the dispersive solution by multiplying a separately determined ratio of a target element to a labeled element in the electrolyte by a labeled element in the dispersive solution and subtracting the product from the amount of target element in the dispersive solution.

18. The method of claim 1, wherein the metal precipitates and inclusions comprise a metal selected from the group consisting of titanium and manganese.

* * * * *